United States Patent
Flanagan et al.

(10) Patent No.: US 9,756,324 B1
(45) Date of Patent: Sep. 5, 2017

(54) SYSTEM AND METHOD FOR COLOR CALIBRATING AN IMAGE

(71) Applicant: GELT Inc., Saugus, MA (US)

(72) Inventors: Mark S. Flanagan, Beverly, MA (US); James Paolino, Somerville, MA (US)

(73) Assignee: GELT Inc., Saugus, MA (US)

( * ) Notice: Subject to any disclaimer, the term of this patent is extended or adjusted under 35 U.S.C. 154(b) by 0 days.

(21) Appl. No.: 15/483,707

(22) Filed: Apr. 10, 2017

(51) Int. Cl.
  *H04N 17/02* (2006.01)
  *G06T 7/80* (2017.01)
  *G06T 7/90* (2017.01)

(52) U.S. Cl.
  CPC .............. *H04N 17/02* (2013.01); *G06T 7/80* (2017.01); *G06T 7/90* (2017.01); *G06T 2207/10024* (2013.01); *G06T 2207/30204* (2013.01)

(58) Field of Classification Search
  USPC ................................................. 382/162, 294
  See application file for complete search history.

(56) References Cited

U.S. PATENT DOCUMENTS

| | | | |
|---|---|---|---|
| 7,581,884 B1 * | 9/2009 | Barnes ..................... | A61B 6/06 378/164 |
| 8,340,415 B2 * | 12/2012 | Hoppe .................. | G06T 3/4007 382/162 |
| 8,916,390 B2 | 12/2014 | Ozcan et al. | |
| 9,210,404 B2 * | 12/2015 | Hall ................... | H04N 13/0246 |
| 9,339,194 B2 * | 5/2016 | Adams ................. | A61B 5/0075 |
| 9,622,821 B2 * | 4/2017 | Gopalakrishna ....... | A61B 6/503 |
| 2008/0240558 A1 | 10/2008 | Li et al. | |

OTHER PUBLICATIONS

Velikova, et al., "Smartphone-based analysis of biochemical tests for health monitoring support at home," Healthcare Technology Letters; Apr. 9, 2014, 6 pages.

Carrio, et al., "Automated Low-Cost Smartphone-Based Lateral Flow Saliva Test Reader for Drugs-of-Abuse Detection," Sensors 2015, 25 pages.

Smith, et al., "Cell-Phone-Based Platform for Biomedical Device Development and Education Applications," PLoS ONE, Mar. 2011, 11 pages.

Tuijn, et al., "Data and Image Transfer Using Mobile Phones to Strengthen Microscopy-Based Diagnostic Services in Low and Middle Income Country Laboratories," PLoS ONE, Apr. 2011, 8 pages.

\* cited by examiner

*Primary Examiner* — Ishrat I Sherali
(74) *Attorney, Agent, or Firm* — Cooley LLP

(57) ABSTRACT

Systems and methods for color calibrating an image are described herein. In some embodiments, a method includes disposing a unique identifier and a fiducial marker that includes a plurality of color regions on an object. A first image of the object is captured with a first camera and a second image of the object that is captured with a second camera is received. The second image is associated with the first image based on the unique identifier and spectral information of at least a portion of the fiducial marker in the second image is compared with spectral information of at least the portion of the fiducial marker in the first image. Based on the comparison, the second image is resampled to substantially match at least the portion of the fiducial marker in the second image to at least the portion of the fiducial marker in the first image.

30 Claims, 5 Drawing Sheets

SYSTEM AND METHOD FOR COLOR CALIBRATING AN IMAGE

BACKGROUND

Embodiments described herein relate generally to systems and methods for color calibrating an image, and in particular to color calibrating an image for qualitative and/or quantitative image analysis.

A wide variety of applications (e.g., medical diagnostics, security, and remote sensing) implement techniques to extract meaningful information from captured images. More specifically, meaningful information can be extracted by analyzing and/or measuring colors in a captured image. However, images are often captured in an uncontrolled manner. That is, images may be captured using different cameras and under different settings (e.g., lighting, fixtures, etc.). So, two cameras capturing an image of the same object may produce different results making it challenging to analyze these images or measure the colors in these captured images.

Hence, there is an unmet need to provide a system and method to control and calibrate an image that is agnostic to the type of camera or the environment in which the image is captured.

SUMMARY

Systems and methods for color calibrating an image are described herein. In some embodiments, a method includes disposing a unique identifier and a fiducial marker that includes a plurality of color regions on an object. A first image of the object is captured with a first camera and a second image of the object that is captured with a second camera is received. The second image is associated with the first image based on the unique identifier and spectral information of at least a portion of the fiducial marker in the second image is compared with spectral information of at least the portion of the fiducial marker in the first image. Based on the comparison, the second image is resampled to substantially match the first image.

In some embodiments, a method includes collecting reliable data relating to a test associated with the diagnostic assay. The method includes disposing a unique identifier on a diagnostic assay, disposing a spectral fiducial that includes a plurality of color regions on the diagnostic assay, and capturing with a first camera a first image of the diagnostic assay. The method further includes at a processor, receiving a second image of the diagnostic assay that is captured with a second camera, associating the second image with the first image based on the unique identifier, comparing spectral information of at least a portion of the spectral fiducial in the second image with spectral information of at least the portion of the spectral fiducial in the first image, resampling the second image to substantially match the first image based on the comparison, and correlating spectral information of at least a portion of the resampled second image to corresponding information relating to the test to collect reliable data.

In some embodiments a system includes a server processor and a manufacturing unit in digital communication with the server processor. The manufacturing unit is configured to (a) dispose a unique identifier on an object, (b) dispose a spectral fiducial on the object, the spectral fiducial including a plurality of color regions, (c) capture a first image of the object with an image capturing device, and (d) transmit the first image to the server processor. The server processor is configured to (a) receive a second image of the object from a remote image capturing device, (b) associate the second image with the first image based on the unique identifier, (c) compare spectral information of at least a portion of the spectral fiducial in the second image with spectral information of at least the portion of the spectral fiducial in the first image, and (d) resample the second image to substantially match the first image based on the comparison.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Figure 1:
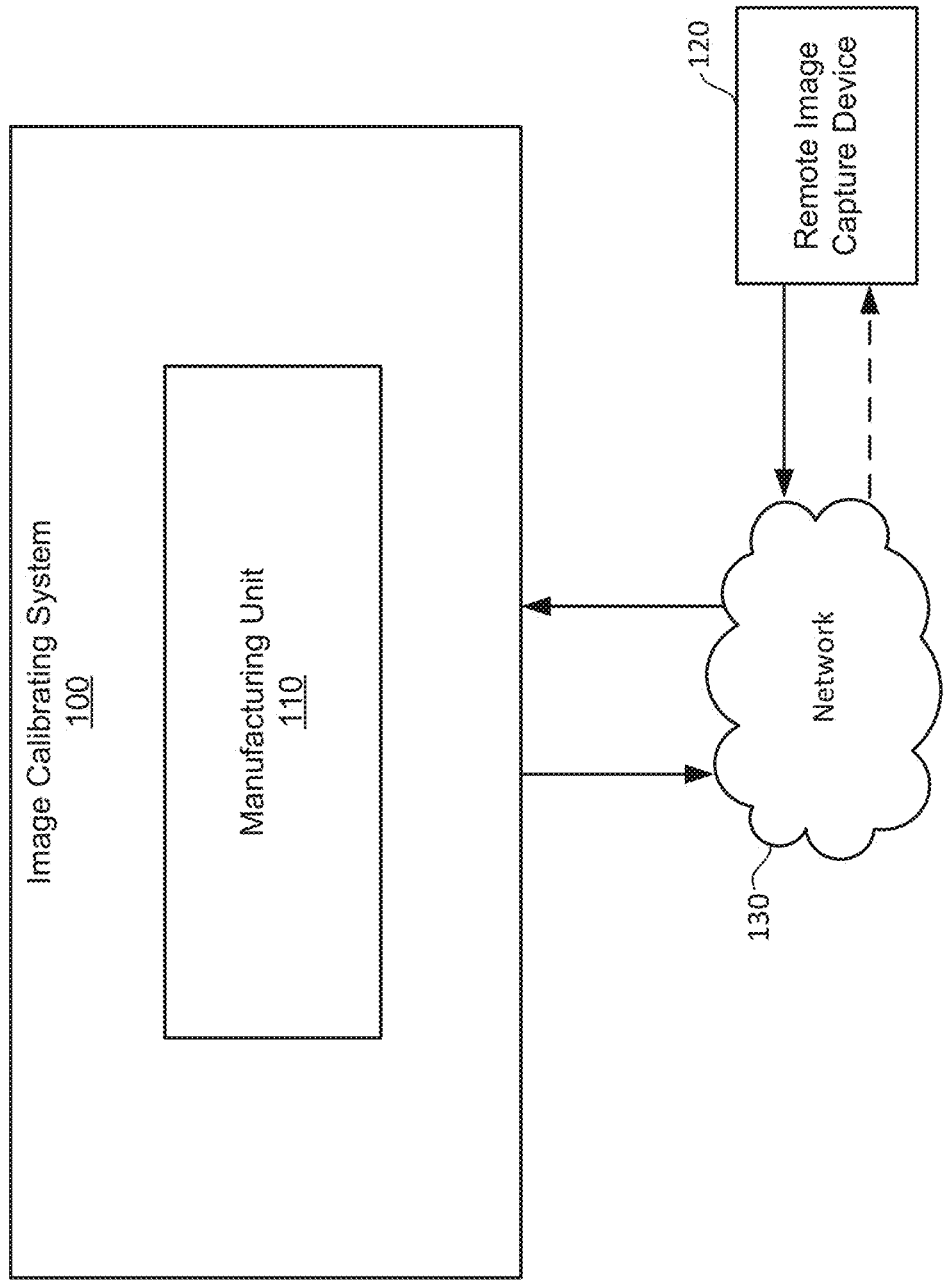
FIG. 1 illustrates an overview of an image calibrating system, according to an embodiment.

The present disclosure describes systems and methods for color calibrating an image in a manner that is agnostic to the type of image capturing device and/or the environment in which the image is captured.

Image-based analysis is often performed to extract meaningful information from captured images. However, images may not always be captured in a standard manner. For example, different cameras can have different settings and/or the users of the cameras can use different positioning or focal points, resulting in vastly different images of the same object. Similarly, the same camera may capture images at a different time with different settings, positioning, focal point, etc. In addition, the environment in which the images are captured can affect the captured image. For example, lighting or shadows can make images that are captured from the same camera seem dramatically different. Thus, two cameras capturing an image of the same object might produce two different results. Likewise, the same camera capturing two different images of the same object at a different time may produce two different results.

Embodiments described herein disclose systems and methods to modify a captured image irrespective of the type of device used to capture the image or the environment in which the image is taken. In some embodiments, a unique identifier and a fiducial marker (also referred to as "spectral fiducial") are disposed on an object during or after manufacturing of the object. The unique identifier can be used to reference captured images of the object and/or to associate captured images of the object with other images of the object or the object itself. The fiducial marker can be used as a point of reference and/or to calibrate captured images of the object. The facility/unit to manufacture the object can include a first image capturing device. The manufacturing unit with the first image capturing device can be configured to capture an image of the object in a controlled manner. That is, the image is captured with a known image capturing device (first image capturing device) and under known settings. In addition, images of other objects may also be captured using the same image capturing device (first image capturing device) and under the same settings.

The image from the manufacturing unit captured in a controlled manner (also referred to as "pre-image") is transmitted to a processor/server. The server references the pre-image with the unique identifier and stores the pre-image in a database and/or memory. After the pre-image is transmitted from the manufacturing unit to the server, the object is dispatched and is obtained by an end user. The dispatched object may or may not be used by the end user. That is, the end user may change a portion of the object. However, the unique identifier and spectral fiducial disposed on the object does not change significantly. A second image capturing device (also referred to as a "remote image capturing device") associated with the end user can be used to capture an image (i.e., a picture) of the dispatched object. The second image capturing device can be used to capture the image in an uncontrolled manner. More specifically, the second image capturing device can be any type of image capturing device and the image can be captured in under any setting. The image from the second image capturing device captured in an uncontrolled manner (also referred to as "captured image") can then be transmitted to the server.

The server can be configured to access the pre-images stored in the memory and associate the unique identifier in the captured image with the unique identifier in the pre-image. The server can then compare the spectral fiducial and/or a portion of the spectral fiducial in the captured image with the spectral fiducial and/or the corresponding portion of the spectral fiducial in the pre-image. Based on this comparison, the server can be configured to resample the captured image to substantially match the pre-image. In other words, the server can modify the captured images color-correct and/or otherwise modify the captured image such that the color, exposure, white balance, etc. to substantially match the pre-image. In this manner, images captured from an "uncontrolled" camera can be modified as if they were captured in a controlled environment with controlled settings. Reliable information can then be extracted from the resampled captured image. Thus, information from the image can be extracted such that the type of the image capturing device or the environment in which the image is captured does not affect the reliability of the information.

FIG. 1 is a schematic overview of an image calibrating system 100, according to some embodiments. The image calibrating system 100 includes a manufacturing unit/subsystem and/or a production facility 110 that includes a first image capturing device (not shown) a second image capturing device 120, and a server processor 130. The manufacturing unit 110 and the first image capturing device are in digital communication with the server processor 130, and the server processor 130 is in digital communication with the second image capturing device 120. In some embodiments, the manufacturing unit 110 can be a facility and/or system that manufactures the object. In some embodiments, the manufacturing unit 110 can be a facility and/or system that obtains the manufactured object and subsequently applies steps to capture the pre-image of the object as described below.

The manufacturing unit 110 can be configured to provide a unique identifier to an object such that the object, any image of the object and/or any information related to the object can be tracked. The unique identifier can be a barcode, a hologram, magnetic ink characters, combinations thereof, and/or the like. In some embodiments, the unique identifier can be formed by a random pattern of particles disposed on a substrate such as a label. In some embodiments, the unique identifier can be a serialization code, a bar code, a QR code, or a human readable alphanumeric code that is electronically printed on the object. The unique identifier can be disposed on an adhesive label and the adhesive label is disposed on the object. The unique identifier facilitates tracking of the object, images of the object, and/or any information specifically related to the object. In some embodiments, the unique identifier can include anti-counterfeiting measures configured to ensure the authenticity of the object. In some embodiments, the manufacturing unit 110 disposes the unique identifier during the manufacture of the object. In some embodiments, the manufacturing unit 110 disposes the unique identifier following the manufacture of the object.

The manufacturing unit 110 can also be configured to dispose a spectral fiducial on the object such that the spectral fiducial forms a basis for comparing images of the object. In some embodiments, the fiducial marker is a spectrum of colors or a scheme of spectral fiducial. The spectral fiducial can include a plurality of color regions. In some embodiments, the color regions can be separate and distinct. The spectral fiducial can be arbitrary blobs of colors. In some embodiments, the spectral fiducial can include multiple shades of the same color. In some embodiments, the spectral fiducial can include different colors. In some embodiments, one portion of the spectral fiducial can include multiple shades of the same color while a different portion includes different colors. In some embodiments, the fiducial marker can be a grayscale image that is electronically printed on the object. In some embodiments, the fiducial marker can be any arbitrary intrinsic component of the object being imaged. In some embodiments, the manufacturing unit 110 disposes the fiducial marker during the manufacture of the object. In some embodiments, the manufacturing unit 110 disposes the fiducial marker following the manufacture of the object. In some embodiments, the fiducial marker can be disposed on an adhesive label and the adhesive label can be disposed on the object. In some embodiments, the spectral fiducial is printed directly on the object.

As described herein, the spectral fiducial can be utilized to compare and correct images of an object. In some embodiments, the spectral fiducial can be utilized to compare and correct a portion of an image (also referred to as "region of interest" or "ROI"). In other words, the spectral fiducial can be utilized to compare and correct only the region of interest rather than correcting the entire image of the object. In some embodiments, the spectral fiducial can include discreet hues of a single color or a range of colors such that correction of images can be centered around a specific series of wavelengths to provide a more robust and accurate method for correcting spectra within the region of interest to the targeted wavelengths in the spectral fiducial and/or multiple spectral fiducials. Thus, practical constraints of space and resolution can be overcome by utilizing the space available on the image to provide discreet colors such that the targeted spectra within the ROI can be ideally represented.

The manufacturing unit 110 includes a first image capturing device (not shown) that is configured to capture a pre-image of the object. The first image capturing device along with the manufacturing unit 110 can be configured to capture the pre-image of the object in a controlled manner. That is, the manufacturing unit 110 uses a known image capturing device to capture the pre-images under known settings (e.g., controlled lighting and fixtures). Additionally, the same image capturing device can be used to capture pre-images of every object in a stable and controlled environment (e.g., controlled lighting and fixtures). Said another way, a pre-image of every object is captured by the same image capturing device under the exact same setting. In some embodiments, the first image capture device can be configured to take multiple images of the object and the manufacturing unit 110 can be configured to determine which image or images should be stored for later comparison.

In some embodiments, the first image capturing device can be stationary equipment, such as a flat bed scanner. In some embodiments, the first image capturing device can be a portable device such as a handheld computer tablet, a smartphone with camera, or a digital camera. In some embodiments, the first image capturing device includes or is otherwise configured to utilize an adapter or other attachment to a mobile electronic device, such as a phone or tablet, to capture the pre-image. In this manner, at least a portion of the first image capturing device is generally mobile and can easily be transported between and/or around shipping vessels, warehouses, or other locations, for manufacturing objects at various locations in the supply chain. In some embodiments, the first image capturing device can be substantially stationary. The pre-image can be an image of the entire object including the unique identifier and the spectral fiducial. The pre-image is transmitted from the manufacturing unit 110 to the server processor 130. In some embodiments, the manufacturing unit 110 additionally sends information that is necessary for analyzing captured images of the object and for collecting reliable data from captured images (e.g., data relating to calibrating and correcting images).

In some embodiments, the second image capturing device 120 is associated with an end user. In some embodiments, the second image capturing device can be a portable device such as a handheld computer tablet, a smartphone with camera, or a digital camera. In some embodiments, the second image capturing device includes or is otherwise configured to utilize an adapter or other attachment to a mobile electronic device, such as a phone or tablet. In this manner, at least a portion of the second image capturing device is generally mobile and can easily be transported between various locations. In some embodiments, the second image capturing device can be substantially stationary. As described herein, the second image capturing device 120 captures the image in an uncontrolled manner. That is, images are captured using different types of image capturing devices in different settings and thus, the images can be captured in a device and environment agnostic manner. Captured images of the object can be transmitted from the second image capturing device 120 to the server processor 130 for calibration and analysis.

The server processor 130 is in digital communication (e.g., wired or wireless) with the manufacturing unit 110 and the second image capturing device 120. The server processor 130 can be configured to calibrate a captured image. Information (e.g., pre-images and information relating to calibrating captured images) are sent from the manufacturing unit 110 to the server processor 130. The server processor 130 can include at least one storage unit (e.g., memory, database, etc.) to store information obtained from the manufacturing unit 110. In some embodiments, when pre-images are transmitted from the manufacturing unit 110 to the server processor 130, the server processor 130 can be configured to reference the pre-image with the unique identifier disposed on the pre-image. The pre-image is then stored in the storage unit along with the reference.

Upon obtaining a captured image from the second image capturing device 120, the server processor 130 can be configured to access the storage unit to associate the unique identifier in the captured image to the unique identifier in a pre-image. As discussed in greater detail below, the server processor 130 can compare spectral information in the captured image to the spectral information in the pre-image and resample the captured image to substantially match the pre-image. More specifically, the server processor 130 can be configured to compare at least a portion of the spectral fiducial in the captured image to a corresponding portion of the spectral fiducial in the pre-image. The server processor 130 can be configured to resample the captured image based on this comparison such that the spectral fiducial on the captured image substantially matches the spectral fiducial on the pre-image. In some embodiments, the server processor 130 can correlate the colors on the resampled captured image to the spectral fiducial of the resampled captured image. In some embodiments, the server processor 130 can correlate spectral information of the resampled image with the corresponding information specific to the object that was previously transmitted from the manufacturing unit 110 and stored in the storage unit to collect reliable data. The corresponding information can be information relating to calibrating captured images of the object. Some non-limiting examples of spectral information can include intensity, wavelength, spectral value, Doppler shift, Zeeman splitting, combinations thereof, and/or the like. In some embodiments, the server processor 130 is a cloud-based server processor.

Figure 2A:
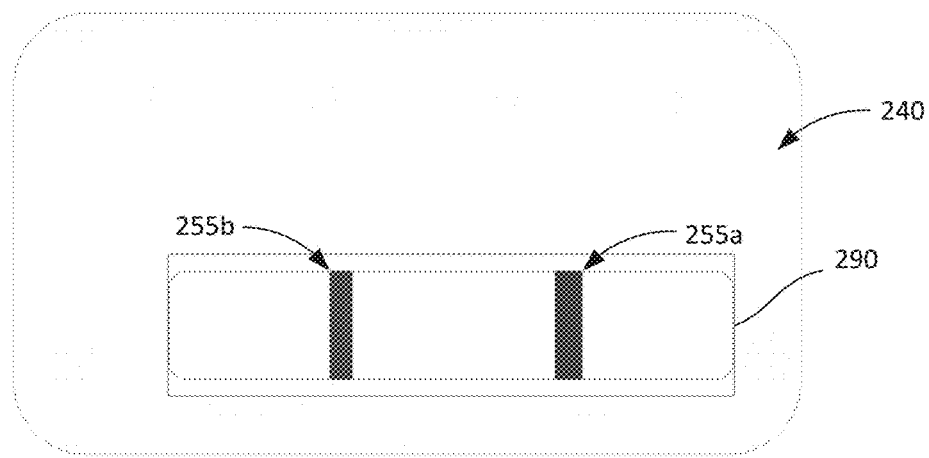
FIGS. 2A-2C illustrate the process of manufacturing an object for image calibration in accordance with some embodiments.
Figure 2B:
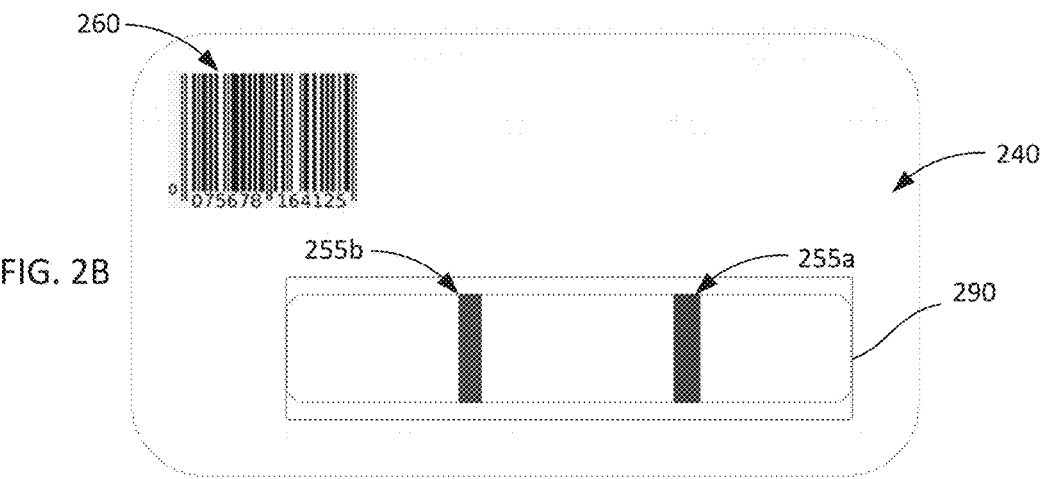
Figure 2C:
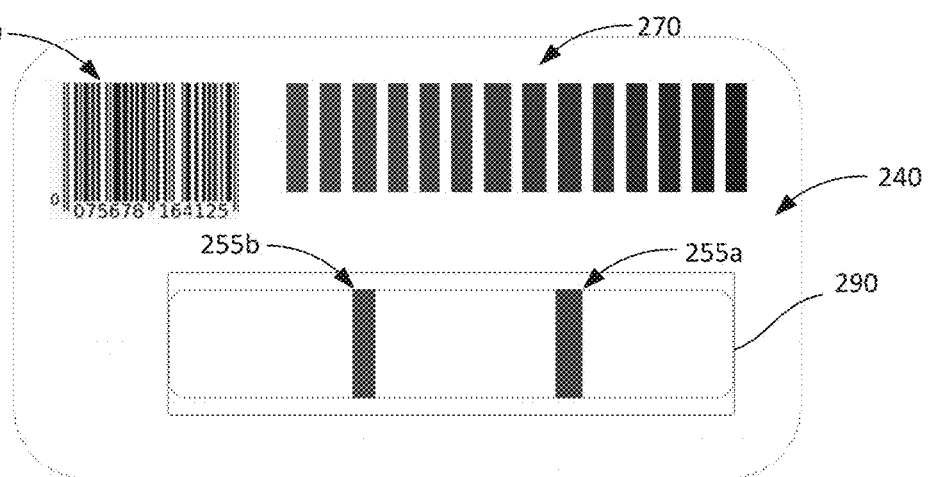

FIGS. 2A-2C illustrate manufacturing of an object 240, according to an embodiment. A manufacturing or production facility (e.g., manufacturing unit 110 in FIG. 1) can be configured to manufacture the object 240. Captured images of the object 240 can be calibrated and analyzed to extract meaningful quantitative and/or qualitative information.

In some embodiments, the object 240 is a diagnostic assay. In some embodiments, the object 240 is a lateral flow immunochromatographic assay intended to detect the presence or absence of an analyte. In some embodiments, the lateral flow immunochromatographic assay can include sample pad, a conjugate pad, a membrane, a wicking pad, a test area 255a, and a control area 255b. An image of a portion 290 of the object 240 including the sample pad, conjugate pad, membrane, wicking pad, test area 255a and control area 255b together form the portion of the image of the object that can be defined as a region of interest. The lateral flow immunochromatographic assay includes a series of capillary beds that transports fluids. The fluid in chemical combination with particles that are already present in the assay are transported through the assay via capillary action. When the fluid passes through the test area 255a and the control area 255b, particles accumulate and the test area 255a and the control area 255b change color. In this manner, the presence or absence of an analyte can be detected by analyzing the color in the test area 255a and the control area 255b. In some embodiments, a color change can simply indicate the presence of an analyte. In other words, some immunochromatographic assays are "binary" in that they are simply configured to detect whether or not an analyte is present or not. In some embodiments, an immunochromatographic assay can be configured to detect the amount of the analyte present. The amount of the analyte present can be determined by measuring the intensity of the color in the test area 255a and the control area 255b.

Referring to FIG. 2A, the object 240 can include a test area 255a and a control area 255b. The test area 255a and the control area 255b in the object 240 can be configured so as to provide qualitative information relating to a specific test. Qualitative information from the object 240 can be extracted based on the color of the test area 255a and the control area 255b. In some embodiments, the intensity of the color in the test area 255a and the control area 255b can be measured to extract quantitative information relating to that specific test. For lateral flow immunochromatographic assays, the color of the test area 255a can be correlated to the amount of analyte present thus providing meaningful quantitative information. Thus, the image of the portion 290 of the object is the ROI that provides meaningful information relating to the specific test.

Referring to FIG. 2B, the manufacturing or production facility can be configured to dispose a unique identifier 260 on the object 240. The unique identifier 260 can be a barcode, a hologram, magnetic ink characters, combinations thereof, and/or the like. In some embodiments, the unique identifier 260 can be formed by a random pattern of particles disposed on a substrate such as a label. In some embodiments, the unique identifier 260 can be a serialization code, a bar code, a QR code, or a human readable alphanumeric code that is electronically printed on the object. The unique identifier 260 can be disposed on an adhesive label and the adhesive label is disposed on the object. The unique identifier 260 facilitates tracking of the object, images of the object, and/or any information specifically related to the object. In some embodiments, the unique identifier 260 can include anti-counterfeiting measures configured to ensure the authenticity of the object.

Referring to FIG. 2C, the manufacturing or production facility can be configured to dispose a spectral fiducial 270 on the object 240. In some embodiments, the spectral fiducial 270 is a spectrum of colors or a scheme of spectral fiducial 270. The spectral fiducial 270 can include a plurality of color regions. In some embodiments, the color regions can be separate and distinct. The spectral fiducial 270 can be arbitrary blobs of colors. In some embodiments, the spectral fiducial 270 can include multiple shades of the same color. In some embodiments, the spectral fiducial 270 can include different colors. In some embodiments, one portion of the spectral fiducial 270 can include multiple shades of the same color while a different portion includes different colors. In some embodiments, the spectral fiducial 270 can be a grayscale image that is electronically printed on the object. In some embodiments, the fiducial marker 270 can be any arbitrary intrinsic component of the object being imaged. In some embodiments, the spectral fiducial 270 can be disposed on an adhesive label and the adhesive label can be disposed on the object. In some embodiments, the spectral fiducial 270 is printed directly on the object.

As described herein, the spectral fiducial 270 can be utilized to compare and correct images of an object. In some embodiments, it may be desirable to only correct an image of a portion of the object 240 (e.g., a region of interest). For instance, in a diagnostic assay or lateral flow immunochromatographic assay, an image of the portion 290 of the assay 240 including the test area 255a and control area 255b can be compared and corrected to extract meaningful information. Thus, the spectral fiducial can be utilized to compare and correct a portion of an image (e.g., ROI) of the assay (e.g., object 240) rather than the entire assay. In order to utilize space available on the object 240, the spectral fiducial 270 can include discreet hues of a single color or a range of colors such that correction of images can be centered around specific series of wavelengths. This provides for a more robust and accurate method as far as correcting spectra within the region of interest to the targeted wavelengths on the spectral fiducial 270. That is, the range of colors and their associated wavelengths can be configured such that targeted portions of the ROI can be compared and corrected in an accurate and robust manner even if the rest of the image may not be corrected accurately.

For example, in a test associated with the diagnostic assay or lateral flow immunochromatographic assay that turns red in the presence or absence of an analyte, the spectral fiducial 270 can be configured such that the discreet colors included in the spectral fiducial 270 are shades and/or hues of red. In such a case, when a captured image of the assay is compared and corrected with the corresponding pre-image based on the spectral fiducial 270, portions of the ROI in the resampled captured image may look slightly different from the pre-image. However, as long as the "reds" in the test area 255a and/or control area 255b are accurately represented, the result of the test will be accurate. Said another way, by targeting only shades/hues of red, the color correction may be less accurate for blue, green, etc. at the expense of accuracy "reds". However, a spectral fiducial of all of the visible colors can result in a poor sample size of "red" colors, so the color correction be less accurate for a particular range of wavelengths (e.g., reds) even though it will generally be more accurate for the broad visible spectrum.

Figure 3:
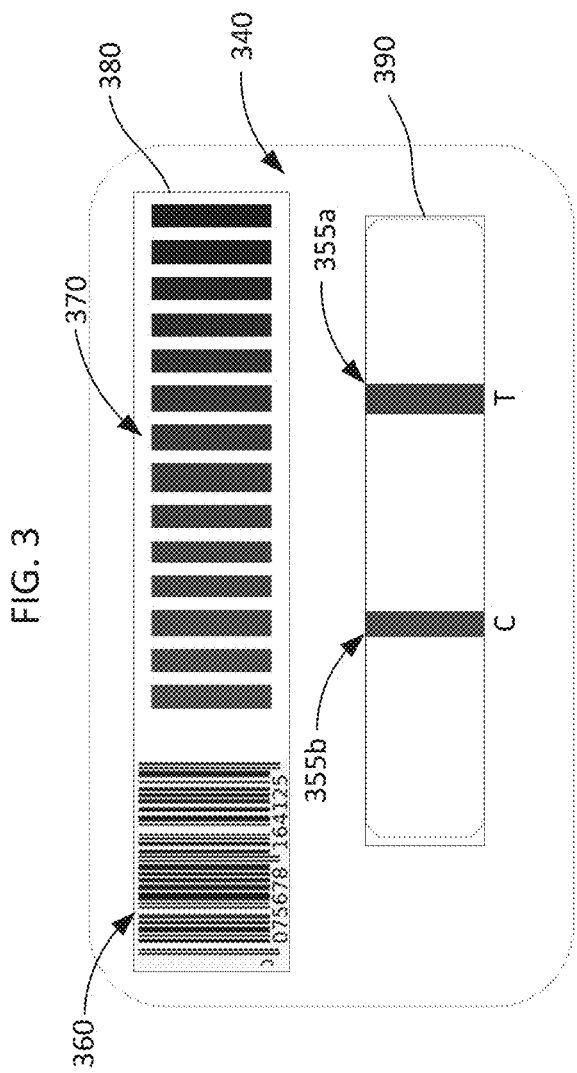
FIG. 3 illustrates a manufactured object for image calibration, according to an embodiment.

Therefore, if a test is configured such that the color change of test area 255a in a particular range of wavelengths indicates analyte concentration (e.g., from light pink when low concentrations of an analyte is present, to a darker red when higher concentrations of the analyte is present) providing a spectral fiducial 270 that includes a variety of shades and/or hues in that particular range of wavelengths can allow for a more accurate color correction of the image. The more accurate color correction of the image can be used to provide a more accurate determination of analyte concentration in the sample. FIG. 3 illustrates an object 340 manufactured at the manufacturing unit 110 in FIG. 1, according to an embodiment. The object 340 includes a unique identifier 360 and a spectral fiducial 370 disposed on an adhesive label 380. The unique identifier 360 can be substantially similar in form and/or function to the unique identifier 260 and thus, some aspects of the unique identifier 360 are not described in further detail herein. Similarly, the spectral fiducial 370 can be substantially similar in form and/or function to the spectral fiducial 270 and thus, some aspects of the spectral fiducial 370 are not described in further detail herein. In some embodiments, the object 340 includes a unique identifier 360 and a spectral fiducial 370 disposed on an adhesive label 380. In some embodiments, the object 340 is a diagnostic assay including a test area 355a and a control area 355b. Qualitative information can be extracted from the object 340 itself or from an image of the object 340 by analyzing and detecting the color of the portion 390 of the object 340 including the test area 355a and/or the control area 355b. As described above, the intensity of the color in the portion 390 of the object 340 that includes the test area 355a and/or the control area 355b can be measured to extract quantitative information by analyzing the object 340 itself or by analyzing an image of the object 340.

Figure 4A:
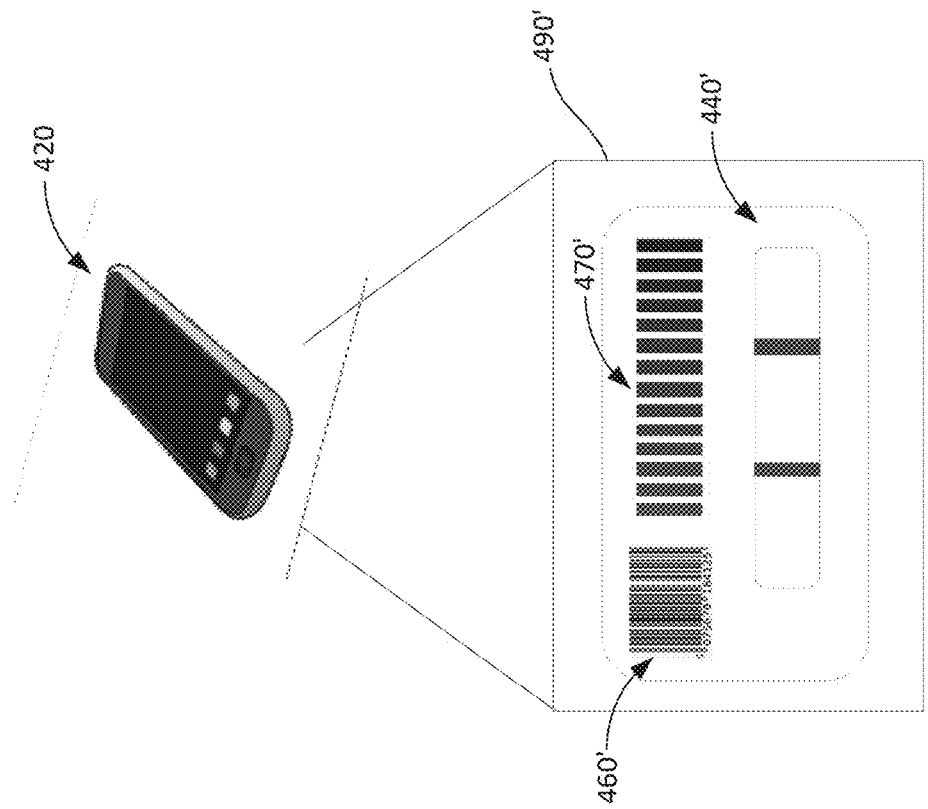
FIGS. 4A-4B illustrate capturing a pre-image and a captured image, according to an embodiment.
Figure 4B:
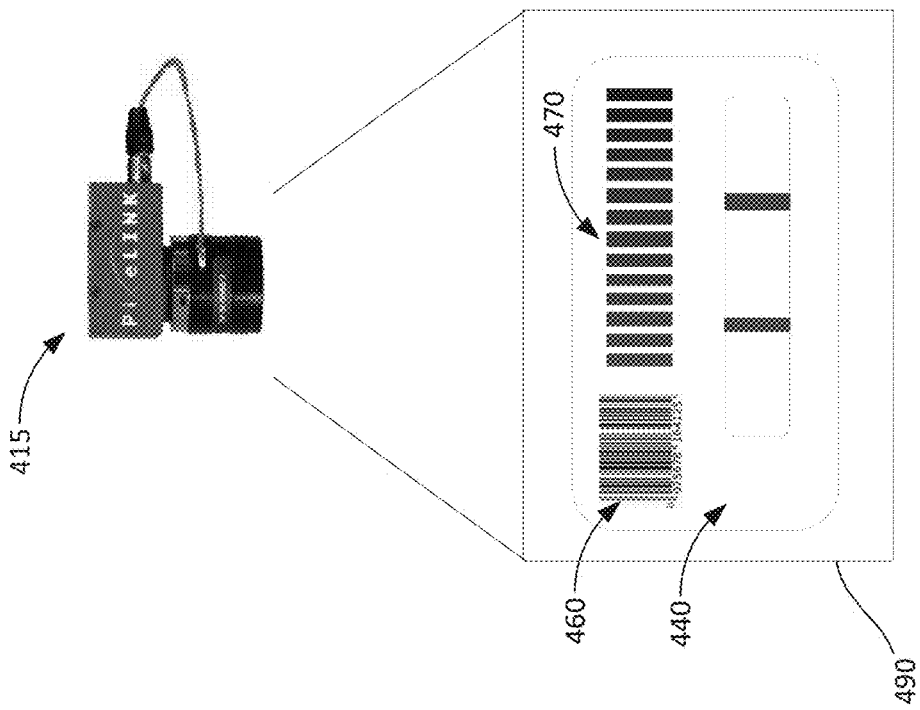

FIGS. 4A and 4B illustrate capturing a pre-image 490 of an object 440 at a first time period and capturing a captured image 490' of the object 440' at a second time period, according to an embodiment. The object 440 and 440' can be substantially similar in form and/or function to the object 240 or 340 and thus, some aspects of the object 440 are not described in further detail herein. A manufacturing or production facility (e.g., manufacturing unit 110 in FIG. 1) can include a first image capturing device 415 configured to capture the pre-image 490 of the object in a controlled manner. That is, the pre-image 490 is captured by a known image capturing device 415 under controlled (i.e., known) settings. The image capturing device 415 can be substantially similar in form and/or function to the image capturing device described above and thus, some aspects of the image capturing device 415 are not described in further detail herein. In addition, all pre-images may be captured by the first image capturing device 415 under same settings/conditions. In some embodiments, the pre-image 490 is the image of the manufactured object 340 in FIG. 3 captured by the first image capturing device 415 at a manufacturing or production facility. The pre-image 490 can be transmitted from the first image capturing device 415 to a server processor (e.g., server processor 130 in FIG. 1). The server processor can be configured to reference the pre-image 490 with a unique identifier 460 on the pre-image 490 and to store the information in a memory and/or a database.

In some embodiments, after the pre-image 490 is transmitted from the manufacturing or production facility to the server processor, the object is dispatched and is obtained by an end user. As shown in FIG. 4B, captured image 490' from a second image capturing device 420 that is associated with the end user can be transmitted to the server processor. The second image capturing device 420 (also referred to as "remote image capturing device") can be substantially similar in form and/or function to the second image capturing device 120 described above and thus, some aspects of the second image capturing device 420 are not described in further detail herein. In some embodiments, the captured image 490' can be the image of the manufactured object 340 in FIG. 3 obtained and/or used by the end user and captured by the second image capturing device 420. Once the captured image 490' is transmitted to the server processor, the server processor can be configured to associate the unique identifier 460' in the captured image 490' with the unique identifier 460 in the pre-image 490 by accessing stored pre-images in the memory and/or database. Additionally, the server processor can compare the spectral fiducial 470' in the captured image 490' with the spectral fiducial 470 in the pre-image 490 to resample the captured image 490' to substantially match the pre-image 490. In this manner, reliable information can be extracted from the captured image 490' such that the environment in which the captured image 490' is taken and the type of the image capturing device does not affect the information that is extracted.

Figure 5:
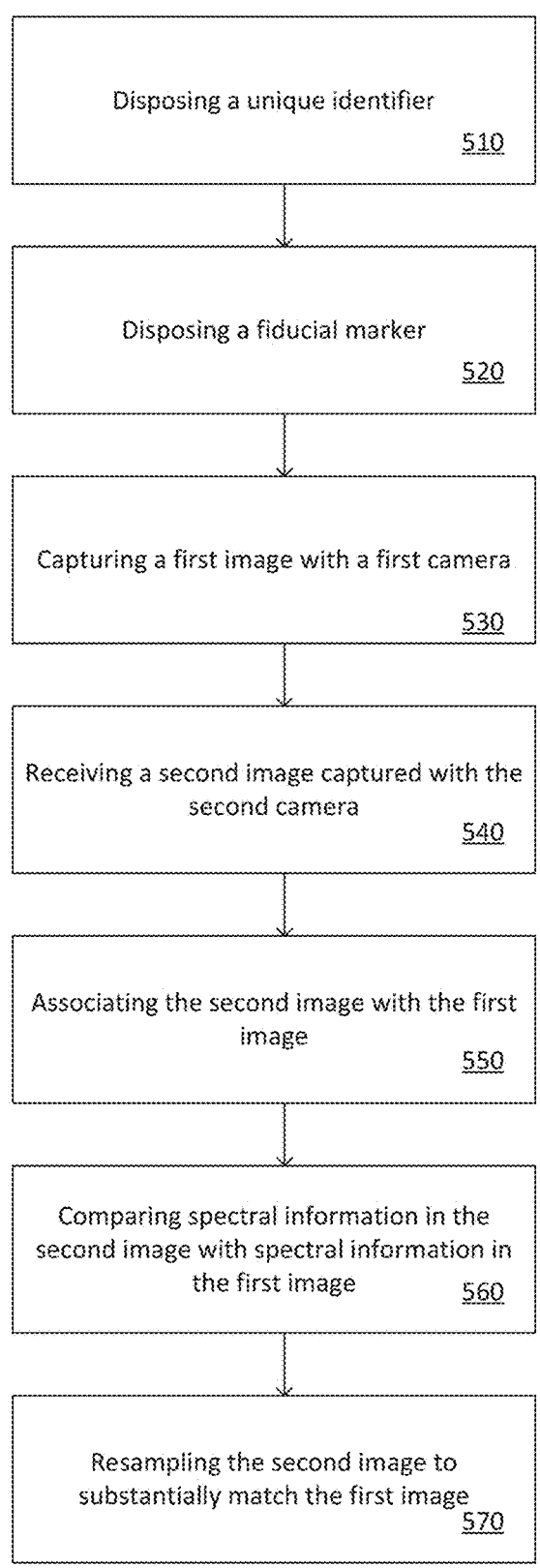
FIG. 5 is a flowchart illustrating a method, according to an embodiment.

FIG. 5 illustrates a method 500, according to an embodiment. In some embodiments, the method 500 is implemented by the image calibrating system 100 disclosed herein. The method 500 includes, at step 510, disposing a unique identifier (e.g., unique identifier 360 in FIG. 3) on an object. At step 520, a fiducial marker (e.g., spectral fiducial 370 in FIG. 3) is disposed on the object. In some embodiments, the fiducial marker is a spectrum of colors or a scheme of spectral fiducial. The spectral fiducial can be arbitrary blobs of colors. At 530, a first image (e.g., pre-image 490 in FIG. 4A) of the object is captured with a first camera (e.g., first image capturing device 415 in FIG. 4A). The first image is captured in a controlled manner. Said another way, the first image is captured by a known first camera and in a known environment. In some embodiments, the spectral values of the colors in the spectral fiducial are printed on the object.

The first image is transmitted to a server system (e.g., server processor 130 in FIG. 1). In some embodiments, the server system is a cloud based server system. The server system references the first image with the unique identifier and stores the first image in a database and/or a memory. At 540, the server system receives a second image (e.g., captured image 490' in FIG. 4B) of the object that is captured with a second camera (e.g., second image capturing device 420 in FIG. 4B). The second image can be captured without qualifying the second camera. That is, the second image can be captured in an uncontrolled manner. At 550, the server system associates the unique identifier on the second image with the unique identifier on the first image by accessing the unique identifier and/or the first image from the database and/or memory. At 560, the server system compares spectral information of the fiducial marker in the second image with spectral information of the fiducial marker in the first image. Some non-limiting examples of spectral information can include intensity, wavelength, spectral value, Doppler shift, Zeeman splitting, combinations thereof, and/or the like. In some embodiments, the server system compares a portion of the fiducial marker in the second image with the corresponding portion of the fiducial marker in the first image. Thus, by analyzing and/or comparing only a portion of the first image and second image, the entire second image can be corrected. At 570, based on the comparison in step 560, the second image is resampled. That is, by comparing at least a portion of the fiducial marker in the second image to the corresponding portion of the fiducial marker in the first image, the fiducial marker in the second image is transformed to substantially match the fiducial marker in the first image. Thus, the entire second image is resampled such that the fiducial marker in the second image substantially matches the fiducial marker in the first image.

In some embodiments, the method 500 can further include correcting the second image for any physical distortions by applying linear transformation of position vectors, such as affine transformation on the second image. The server system can be further configured to linearize the color channels and/or the blobs of colors in the spectral fiducial by applying linear transformation on the spectral fiducial portion of the second image.

In some embodiments, the object is a diagnostic assay and the server system can be configured to analyze the second image to collect quantifiable data relating to a test associated with the diagnostic assay. The diagnostic assay can be an immunochromatographic assay that is used for home testing, point of care testing, laboratory testing, and/or a combination thereof. The diagnostic assay can include sample pad, conjugate pad, membrane, wicking pad, test area, and control area. In some embodiments, information relating to the test (e.g., test values) are stored in the database and/or memory of the server system. The server system can be configured to extract quantifiable data from the second image by correlating the information relating to the test with the resampled second image. For instance, the server system can apply curve fitting formula on the region of interest including the test area and the control area in the resampled second image. By applying the curve fitting formula, the sever system can correlate the spectral information in the resampled second image (e.g., ROI of the resampled second image) with the corresponding information relating to the test (e.g., test values etc.) that is stored in the database and/or the memory. For example, for a diagnostic assay, resampling can include correlating the spectral information in the ROI with properties of an analyte that may have influenced the spectral content of the ROI. In some embodiments, resampling can include color correction, white/gray balancing, gamma correction, affine image transformation (e.g., scale, shear, rotation, and translation), combinations thereof, and/or the like.

In some embodiments, the second camera can include a software to guide an end user to capture the second image. The software may ensure that the second image meets a minimum quality before transmitting the second image to the server system.

In this manner, reliable actionable data can be collected from an image without qualifying the device with which the image is captured. Thus, the color calibration technique disclosed herein is not affected by camera to camera variability or the environment in which an image is captured.

Some embodiments described herein relate to a computer storage product with a non-transitory computer-readable medium (also referred to as a non-transitory processor-readable medium) having instructions or computer code thereon for performing various computer-implemented operations. The computer-readable medium (or processor-readable medium) is non-transitory in the sense that it does not include transitory propagating signals (e.g., a propagating electromagnetic wave carrying information on a transmission medium such as space or a cable). The media and computer code (also referred to herein as code) may be those designed and constructed for the specific purpose or purposes. Examples of non-transitory computer-readable media include, but are not limited to: flash memory, magnetic storage media such as hard disks, optical storage media such as Compact Disc/Digital Video Discs (CD/DVDs), Compact Disc-Read Only Memories (CD-ROMs), magneto-optical storage media such as optical disks, carrier wave signal processing modules, and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages and/or other development tools.

Where methods and/or schematics described above indicate certain events and/or flow patterns occurring in certain order, the ordering of certain events and/or flow patterns may be modified. Additionally certain events may be performed concurrently in parallel processes when possible, as well as performed sequentially.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method comprising:
   disposing a unique identifier on an object;
   disposing a fiducial marker on the object, the fiducial marker including a plurality of color regions;
   capturing a first image of the object with a first camera;
   receiving a second image of the object, the second image captured with a second camera;
   associating the second image with the first image based on the unique identifier;
   comparing spectral information of at least a portion of the fiducial marker in the second image with spectral information of at least the portion of the fiducial marker in the first image; and
   resampling the second image to match at least the portion of the fiducial marker in the second image to at least the portion of the fiducial marker in the first image based on the comparison.

2. The method of claim 1, further comprising:
   storing the first image in a cloud based server system; and
   referencing the first image in the cloud based server system with the unique identifier.

3. The method of claim 1, wherein disposing the fiducial marker includes printing the plurality of color regions on the object.

4. The method of claim 1, further comprising:
   correcting the second image for any physical distortion; and
   quantifying and correlating the second image with respect to the first image.

5. The method of claim 4, wherein correcting the second image includes applying via a cloud based server system, linear transformation of position vectors on the second image.

6. The method of claim 4, wherein linearizing the plurality of color regions includes applying via a cloud based server system, linear transformation on at least the plurality of color regions of the second image.

7. The method of claim 1, wherein the object is a diagnostic assay.

8. The method of claim 7, further comprising:
   analyzing the second image to collect quantifiable data from the second image, the quantifiable data relating to a test associated with the diagnostic assay.

9. The method of claim 1, wherein the fiducial marker is an adhesive label including the plurality of color regions.

10. The method of claim 1, wherein the unique identifier is at least one of a barcode, a hologram, and magnetic ink characters.

11. The method of claim 1, wherein the first image is captured under controlled conditions.

12. The method of claim 1, wherein spectral information includes at least one of intensity, wavelength, spectral value, Doppler shift, and Zeeman splitting.

13. The method of claim 1, wherein resampling the second image includes at least one of color correction, white balancing, gray balancing, gamma correction, and affine image transformation.

14. A method for collecting reliable data relating to a test from a second image, the method comprising:
   disposing a unique identifier on a diagnostic assay;
   disposing a spectral fiducial on the diagnostic assay, the spectral fiducial including a plurality of color regions;
   capturing a first image of the diagnostic assay with a first camera;
   at a processor:
      receiving the second image of the diagnostic assay, the second image captured with a second camera;
      associating the second image with the first image based on the unique identifier;
      comparing spectral information of at least a portion of the spectral fiducial in the second image with spectral information of at least the portion of the spectral fiducial in the first image;
      resampling the second image to match at least the portion of the spectral fiducial in the second image to at least the portion of the spectral fiducial in the first image based on the comparison; and
      correlating spectral information of at least a portion of the resampled second image to corresponding information relating to the test to collect reliable data, wherein the test is associated with the diagnostic assay.

15. The method of claim 14, wherein the diagnostic assay is a lateral flow immunochromatographic assay.

16. The method of claim 14, wherein the spectral fiducial is an adhesive label including the plurality of color regions.

17. The method of claim 15, wherein the lateral flow immunochromatographic assay includes a control area and a test area.

18. The method of claim 17, wherein the at least a portion of the resampled second image is the test area in the resampled second image.

19. The method of claim 15, wherein the lateral flow immunochromatographic assay is a medical diagnostic assay used for at least one of home testing, point of care testing, and laboratory testing.

20. The method of claim 14, wherein spectral information includes at least one of intensity, wavelength, spectral value, Doppler shift, and Zeeman splitting.

21. The method of claim 14, wherein resampling the second image includes at least one of color correction, white balancing, gray balancing, gamma correction, and affine image transformation.

22. The method of claim 14, further comprising:
   correcting the second image for any physical distortion; and
   quantifying and correlating the second image with respect to the first image.

23. The method of claim 22, wherein correcting the second image includes applying via the processor, linear transformation of position vectors on the second image.

24. The method of claim 22, wherein linearizing the plurality of color regions includes applying via the processor, linear transformation on at least the plurality of color regions of the second image.

25. The method of claim 14, wherein correlating includes applying a curve fitting formula on spectral information of the at least a portion of the resampled second image.

26. The method of claim 14, wherein the unique identifier is at least one of a barcode, a hologram, and magnetic ink characters.

27. The method of claim 14, wherein the first image is captured under controlled conditions.

28. The method of claim 14, further comprising:
storing the first image in a cloud based server database.

29. The method of claim 14, wherein the reliable data includes specification, label, and quantity of an analyte.

30. The method of claim 14, wherein the processor is a cloud based server processor.

\* \* \* \* \*